United States Patent
Guracar (10) Patent No.: US 9,066,674 B2
(45) Date of Patent: Jun. 30, 2015

(54) MOTION SYNCHRONIZED DESTRUCTION FOR THREE-DIMENSIONAL REPERFUSION MAPPING IN MEDICAL DIAGNOSTIC ULTRASOUND IMAGING

(75) Inventor: Ismayil M. Guracar, Redwood City, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 402 days.

(21) Appl. No.: 12/726,260

(22) Filed: Mar. 17, 2010

(65) Prior Publication Data

US 2011/0230765 A1 Sep. 22, 2011

(51) Int. Cl.
- A61B 8/00 (2006.01)
- A61B 8/06 (2006.01)
- A61B 8/08 (2006.01)

(52) U.S. Cl.
CPC . *A61B 8/06* (2013.01); *A61B 8/481* (2013.01); *A61B 8/483* (2013.01)

(58) Field of Classification Search
USPC .......... 600/407, 437, 438, 443, 454, 458
See application file for complete search history.

(56) References Cited

U.S. PATENT DOCUMENTS

| | | | |
|---|---|---|---|
| 5,860,931 A * | 1/1999 | Chandler | 600/458 |
| 6,436,045 B1 | 8/2002 | Rafter et al. | |
| 6,494,841 B1 | 12/2002 | Thomas et al. | |
| 6,602,195 B1 | 8/2003 | Krishnan et al. | |
| 6,632,177 B1 | 10/2003 | Phillips et al. | |
| 6,682,482 B1 | 1/2004 | Krishnan | |
| 6,969,353 B2 | 11/2005 | Brock-Fisher et al. | |
| 7,087,023 B2 | 8/2006 | Daft et al. | |
| 7,727,154 B2 | 6/2010 | Kato | |
| 7,837,626 B2 | 11/2010 | Chomas et al. | |
| 8,036,437 B2 | 10/2011 | Arditi et al. | |
| 8,668,648 B2 | 3/2014 | Guracar | |
| 2005/0131300 A1* | 6/2005 | Bakircioglu et al. | 600/453 |
| 2008/0125657 A1 | 5/2008 | Chomas et al. | |
| 2008/0214934 A1 | 9/2008 | Lee et al. | |
| 2010/0069754 A1* | 3/2010 | Raju et al. | 600/439 |

OTHER PUBLICATIONS

U.S. Appl. No. 12/637,493, filed Dec. 14, 2009.
Hansen, C., Hüttebräuker, N., Wilkening, W., Ermert, H., *A Method to Expedite Data Acquisition for Multiple Spatial-Temporal Analyses of Tissue Perfusion by Contrast-Enhanced Ultrasound*, IEEE Trans Ultrason Ferroelectr Freq Control, Mar. 2009, 56(3):507-19.

(Continued)

*Primary Examiner* — Mark Remaly (57) ABSTRACT

Destruction for reperfusion in medical diagnostic ultrasound is synchronized to motion. Perfusion data for a volume is acquired sequentially for different segments of the volume. For a given segment, such as a planar region, motion tracking within the segment is performed. If sufficient registration or correlation exists at the completion of a sequence of scans for the current segment, then a lesser amount of movement is occurring. At this point, the transmission of contrast agent destructive acoustic energy is performed in the next segment. Tracking is repeated for the next segment to synchronize the switch to yet another segment. Other regions for tracking can be used. By controlling transmission of destruction pulses, more reliable perfusion quantities in a volume may be determined.

20 Claims, 1 Drawing Sheet

(56) References Cited

OTHER PUBLICATIONS

Pollard, R., Dayton, P., Watson, K., Hu, X., Guracar, I., Ferrara, K., *Motion Corrected Cadence CPS Ultrasound for Quantifying Response to Vasoactive Drugs in a Rat Kidney Model*, Urology, Sep. 2009, 74(3): 675-681.

Loveless, M., et al. *A Method for Assessing the Microvasculature in a Murine Tumor Model Using Contrast-Enhanced Ultrasonography*, 2008 by the American Institute of Ultrasound in Medicine, J Ultrasound Med 27: 1699-1709, 0278-4297. Abstract only.

Chinese Office Action dated Jan. 23, 2014 from counterpart Chinese application No. 201110113283.7, 13 pgs (with translation).

English translation of Office Action in counterpart German application No. 10 2011 014 301.7, dated May 20, 2014, 8 total pages.

English translation of Office Action in counterpart Japanese application No. 2011-57975, dated Oct. 17, 2014, 3 total pages.

* cited by examiner

MOTION SYNCHRONIZED DESTRUCTION FOR THREE-DIMENSIONAL REPERFUSION MAPPING IN MEDICAL DIAGNOSTIC ULTRASOUND IMAGING

BACKGROUND

The present embodiments relate to reperfusion mapping. In particular, destruction timing is provided for three-dimensional reperfusion qualitative or quantitative analysis.

Three-dimensional perfusion parametric images of ultrasound contrast agents are useful for studying variations in blood flow in organs and tissues in response to disease states, drugs, or other physiological conditions. Destruction-reperfusion sequencing is a well known technique for measuring contrast agent perfusion within an organ or other tissue. For volume perfusion parametric imaging, contrast agent is introduced into the bloodstream and then a region of agent in a cross-section plane is destroyed with high energy ultrasound. The region is then imaged in a non-destructive contrast sensitive mode to measure blood perfusion parameter, such as contrast agent arrival time, maximum intensity projection, normalized time integral, or maximum area coverage. A collection of planar cross sections acquired in sequence can be combined to form a volume data set.

The individual planar cross-sections are formed from a mechanically translated one-dimensional array or from a fully electronically scanned two-dimensional array. In one example, a one-dimensional array is mechanically translated in elevation to create a series of two-dimensional images of a destruction-reperfusion contrast agent arrival time parameter. Each two-dimensional image is individually motion compensated over the destruction-reperfusion cycle for the plane. The collection of two-dimensional images representing the arrival time or rate of perfusion for individual elevation slices are then combined to form the volume data set. The volume data set is used for rendering in three-dimensional or for multiplanar reformatting. However, if there is significant motion during consecutive slice acquisition periods, then the synthesized volume image may not be an accurate representation of the three-dimensional perfusion parameters. Out-of-plane motion may cause geometric distortion and regions which may be skipped or rescanned.

Destruction energy may be steered in response to motion so that the desired region experiences the required destruction energy, and the same region is then tracked and measured during the reperfusion phase. However, this approach may require that the destruction energy be steered in potentially arbitrary directions. The arbitrary direction may be difficult or unattainable for certain object and probe geometries. In addition, some transducers cannot easily scan arbitrary planes and are limited to orthogonally placed line sequences. Arbitrary positioning is difficult with a mechanically translated 1D array since transducer positioning cannot be accomplished at a high frame rate (i.e. 10 Hz) due to mechanical inertia of the transducer and positioning apparatus.

BRIEF SUMMARY

By way of introduction, the preferred embodiments described below include methods, systems, computer readable media, and instructions for motion synchronized destruction for reperfusion in medical diagnostic ultrasound. Perfusion data for a volume is acquired sequentially for different segments of the volume. For a given segment, such as a planar region, motion tracking within the segment is performed. If sufficient registration or correlation exists at the completion of a sequence of scans for the current segment, then a lesser amount of movement is occurring. At this point, the transmission of contrast agent destructive acoustic energy is performed in the next segment. Tracking is repeated for the next segment to synchronize the switch to yet another segment. Other regions for tracking can be used. By controlling transmission of destruction pulses to times of lesser motion or greater registration with a starting state, more reliable perfusion quantities in a volume may be determined.

In a first aspect, a method is provided for motion synchronized destruction for reperfusion in medical diagnostic ultrasound. A sequence of ultrasound frames of data, representing, at least in part, information from contrast agents in a three-dimensional region of a patient is acquired. A registration between data from different times within the sequence is determined. At a time during the sequence, acoustic energy with an amplitude for destruction of the contrast agents is transmitting. The transmitting is synchronized with the registration such that the transmitting occurs where the registration is above a first level and does not occur where the registration is below the first level. An image is generated as a function of a level of contrast agent after the transmitting.

In a second aspect, a computer readable storage medium has stored therein data representing instructions executable by a programmed processor for motion synchronized destruction for reperfusion in medical diagnostic ultrasound. The storage medium includes instructions for generating acoustic energy for destruction of contrast agents, the generating being sequentially performed for different segments of a three-dimensional volume of a patient, obtaining ultrasound data representing reperfusion of contrast agents within each of the different segments, the obtaining for each segment being performed after the generating for the respective segment, and controlling the generating of the acoustic energy for destruction for each segment based on an amount of similarity of the ultrasound data obtained at different times.

In a third aspect, a method is provided for motion synchronized destruction for reperfusion in medical diagnostic ultrasound. With ultrasound from a transducer, first and second different portions of a volume of a patient are scanned. The first portion is scanned a first plurality of times, and then the second portion is scanned a second plurality of times. Contrast agents in the first portion are destroyed prior to the scanning of the first plurality of times. Contrast agents in the second portion are destroyed prior to the scanning of the second plurality of times and after the scanning of the first portion. Data from the first plurality of scans is correlated. The destroying of the contrast agents in the second portion is performed where the correlating indicates a correlation.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In one example embodiment, a collection of two-dimensional ultrasound contrast parametric imaging slices are acquired in destruction-reperfusion sequences. A collection of volume segments, such as two-dimensional slices, of reperfusion related parameters are sequentially acquired. The imaging slices from the different sequences are combined to form a three-dimensional data set. Motion compensation can be used to correct for motion within the two-dimensional slice acquisition, but full motion compensation across two-dimensional slices may not be practical. To reduce or minimize errors due to out-of-plane motion, motion tracking is used to synchronize the destruction events. Destruction is held off until correct registration is achieved between two-dimensional slice acquisitions within a sequence. In other embodiments, three-dimensional tracking is performed, but for segments or other sub-regions in the volume.

The timing of destruction events is synchronized to ensure achievement of accurate spatial alignment of measured segments into a final volume image. For example, blood flow related parameters for a single two-dimensional slice are acquired over a destruction-reperfusion interval with a mechanically translated array with motion tracking. The first frame after destruction is used for tracking purposes during the interval so that motion in plane is compensated. Motion out of plane may cause poor correlation. The switch to the next segment is synchronized with the correlation such that less movement has occurred when transitioning to an adjacent segment of the volume to acquire another sequence for perfusion measurements.

Measurements for a given slice and corresponding scan sequence are performed using a non-destructive or lesser-destructive contrast agent imaging mode, such as cubic fundamental or low mechanical index imaging. The scan sequence for a given segment may occur over many seconds, such as 1 to 30 seconds. The period is consistent with the time for contrast agent to reperfuse a tissue region. A parametric image is formed from this set of two-dimensional measurements. Arrival time is an example of one type of parametric image.

The sequential scanning with destruction synchronization may operate with mechanically translated one-dimensional arrays or fully electronic two-dimensional arrays. Using the tracking, two-dimensional slice or sub-volume measurements may be discarded or not used for perfusion parameter calculation when excessive motion between destruction event and reperfusion measurements occurs. Data associated with poorly correlated scans may not be integrated in perfusion calculation, avoiding corruption of overall measurement.

Figure 1:
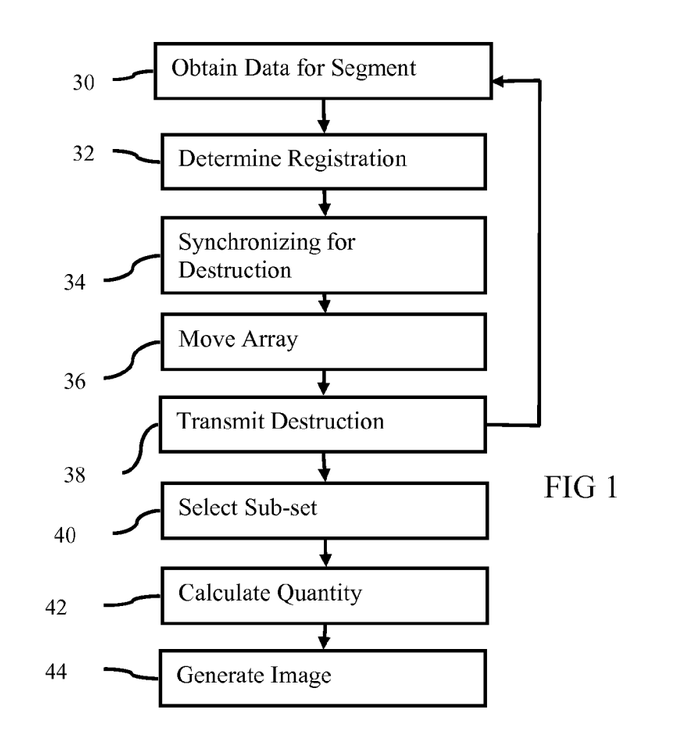
FIG. 1 is a flow chart diagram of a method for motion synchronized destruction for reperfusion in medical diagnostic ultrasound according to one embodiment.

FIG. 1 shows a method for motion synchronized destruction for reperfusion in medical diagnostic ultrasound. The method is implemented by the system 10 of FIG. 2 or a different system. The method is performed in the order shown or a different order. Additional, different, or fewer acts may be provided. For example, act 36 is not performed. Instead, the scan region is moved without movement of the array. As another example, acts 40, 42, 44, and/or 46 are not performed.

In act 30, ultrasound data representing reperfusion of contrast agents is obtained. A sequence of ultrasound frames of data is generated after having destroyed contrast agents or before perfusion by contrast agents. The sequence is generated by acquiring frames of data with ultrasound, or by acquiring previously generated frames of data (e.g., DICOM images). The frames of data are acquired in real time with live scanning or are from stored clips. The sequence may be substantially continuous or periodic (e.g., acquired once or more every heart cycle).

The sequence includes frames of data representing a scanned region at different times. Each frame of data represents a same or overlapping region. Some frames may represent different regions, such as due to out-of-plane motion of the transducer relative to the patient. A frame of data is a group of data representing a complete scan at a given time of a one, two, or three-dimensional region. For example, a frame of data is obtained from a linear, Vector®, sector or segment. As another example, a frame of data represents a sub-volume, such as a conical or cylindrical region within the overall volume to be imaged. The frame of data is samples of a segment or sub-section of the volume to be repetitively scanned for reperfusion.

A sequence of frames of data is acquired for each of different segments of the volume. Within each of the different segments, data is obtained prior to obtaining data for the next segment. A sequence of ultrasound frames of data representing, at least in part, information from contrast agents in each segment is acquired sequentially among the segments. Ultrasound from a transducer is used to sequentially acquire frames of data from different portions of a volume of a patient. One portion is scanned a plurality of times, and then another portion is scanned a plurality of times to provide sequences of frames for different segments.

By acquiring a sequence for each segment sequentially, data representing a volume is obtained. The segments are different portions of the volume so represent the three-dimensional region of the patient in combination. The collection of measurements from a number of small volumes or planes is then combined to produce a full volume parametric image. A collection of volume segments of reperfusion related parameters are acquired where the destruction for each volume segment is synchronized or held off until correct registration occurs. Another motivation for making destruction-reperfusion measurements over small regions is that measurements of local perfusion may be the most diagnostically useful. By destroying agent in a segment, reperfusion for the segment from nearby reservoirs of blood is measured. Destroying agent in a large region may not tell as much about how blood is supplied locally.

In one embodiment, the segment is a planar region of the volume. Ultrasound frames of data are acquired sequentially for different planes in the volume. The sequences for different segments are separated temporally by the transmission or transmissions of act 38. A given sequence for a segment is acquired after destruction of at least some of the contrast agents in the segment.

The different segments are scanned with a mechanically translated one-dimensional array. The array uses a stepper or other motor to move from one position to another position. At each position, a different sequence associated with a segment is obtained. The different segments are different planes defined, at least in part, by the position of the array along the elevation or mechanically scanned dimension.

In another embodiment, the segments are planes or non-planar regions. A multi-dimensional array of elements is used to acquire the sequences. The multi-dimensional array, such as a 2D array, is electronically steered in azimuth and elevation dimensions. The scan lines may be determined by delays and/or apodization. Ultrasound data is obtained using acoustic energy generated with electrical steering in azimuth and elevation directions. The steering directs the scan to sample within a given segment. The array may be moved or held in place. The steering allows scanning of different segments and different scan lines within a given segment.

The volume region of the patient and/or the segment being scanned includes contrast agents or an area likely to include contrast agents after arrival of the agents. The contrast agents respond to ultrasound energies. Some or all of the frames of data include information from contrast agents. The information may also include response from tissue or fluids. In one embodiment, the information is obtained at a cubic fundamental of ultrasound signals. For example, ultrasound signals are transmitted in a plurality of pulses having at least two different amplitude levels and phases. To avoid or minimize destruction of the contrast agents, low amplitude transmissions (e.g., MI less than 0.7) are used. Signals responsive to the transmissions are combined. Data is acquired at each spatial location of a region of interest in each frame of data.

Only one type of data is represented in the frames of data, such as data representing just contrast agents or responses from contrast agent and tissue. Alternatively, the frames of data represent different types of data, such as in a same frame or in different sets of frames.

Each sequence lasts a period, such as 1-30 seconds. Two or more (e.g., tens or hundreds) frames are acquired in each sequence. The period may be based on the reperfusion. For example, the sequence continues until a sufficient contrast agent response is obtained. An average return, or change in average return, area or volume of return, change in area or volume of contrast agent return or other indicator may be used to indicate sufficient reperfusion. User input may indicate completion of the period. The period may be based on a timer, such as a time set for 1-30 seconds from transmission of destruction pulses in act 38.

The period may be based on a physiological cycle. For example, the frames for a segment are acquired over a complete physiological cycle. A breathing cycle may be two or more seconds in length, so the sequence may be greater than two seconds. Breathing may cause patient and/or transducer motion. The patient's skin or body moves due to breathing. The sonographer's hand may move due to breathing. By acquiring over a sequence based on the breathing cycle, variation in registration due to breathing or other physiological related motion may result. By having the period at or about one or more complete cycles, the variation between segments may be reduced.

Correct registration may occur when the tissue under measurement moves back to an original position. The tissue is subject to periodic motion caused by breathing, cardiac motion, peristalsis or other voluntary or involuntary motion of the body being measured or the person holding the transducer. Using the registration of act 32 and the synchronization of act 34, this registration may be used to time the switch to scan another segment at a time of the tissue being in an original position.

In other embodiments, the period is based on a combination of factors. For example, the period is sufficiently long to allow reperfusion. The period is based on ultrasound measurements and/or timed. Once a sufficient length has past, the registration of act 32 and synchronization of act 34 is used to determine the end of the period. The time with sufficient registration after sufficient length is selected as the end of the period and a time to begin scanning a different segment.

In act 32, a registration is determined. The registration is between frames for a given segment. The segment is the same or different one for which a current sequence is acquired for perfusion analysis. In one embodiment, the registration is performed using the frames also being acquired for perfusion analysis. For example, the segment is a planar region. The registration is performed between frames for the same planar region. The registration is a one or two-dimensional registration along one or more dimensions.

Registration is any now known or later developed motion tracking or similarity measure. Data from different scans is correlated. For example, a minimum sum of absolute differences, other sum of absolute differences, cross-correlation, or auto-correlation is used.

The similarity is measured between entire frames (i.e., the entire scan region) or a sub-set. For example, a window from a reference frame is compared to a window for another frame or all of the other frames. The window is a center region, other region of interest, down sampled frame, multiple regions associated with features or peak returns, or other sub-set of the entire frame. The reference frame is a first frame acquired after destruction of contrast agents, an average of a plurality of frames, a template frame, or other frame in a sequence. In one embodiment, a region about ⅔ of the entire area represented by the frame is used as a window in the first frame acquired after destruction of contrast agents for the segment. Other size regions of interest or windows may be used. Subsequent frames are compared to the window to measure similarity.

In alternative embodiments, the motion is tracked and the frames are aligned to correct for inter-frame motion. The similarity is measured between the motion corrected frames of data. In other alternative embodiments, the similarity may be measured as a displacement and/or rotation for a best match between frames. The registration is represented by the amount of displacement and/or rotation.

The registration indicates a level of transducer movement, patient movement, organ movement, combinations thereof, or other motion. Global or local motion may be determined.

When the segment being scanned switches, the registration is switched to data for the new segment. A new reference frame of data is selected and registration for the new segment is performed with the new reference frame of data.

The similarity may be a three-dimensional similarity, such as determining an amount of registration between frames for a given sub-volume of the entire three-dimensional region of the patient being studied. The sub-volume is a segment. Registration may be based on the data for the entire sub-volume or less than the entire sub-volume. Instead of individual two-dimensional slices, small regions or sub volumes are measured for similarity. For example, contrast agents in a small cylindrical region are destroyed. Reperfusion analysis for a smaller, local region may provide a better measure of perfusion capacity of a given tissue. Tracking on this small sub-volume may be performed during the reperfusion integration phase.

In one embodiment, the characteristic for registration relates to or is derived from the same type of data to be used for perfusion analysis. In another embodiment, characteristics of at least a first type of data are used for the registering, and data of at least a second type of data is used for perfusion analysis. For example, several clinical ultrasound images or frames of data with mixed contrast agent type data and B-mode type data are used—the B-mode or more tissue responsive data used for registration and the contrast agent or more contrast agent responsive data used for perfusion study. The different types of data represent the same or overlapping regions at a same or substantially same time.

In act 34, the generation of the acoustic energy for destruction is controlled. Once a complete set of frames of data for perfusion of a segment is acquired in act 30, the perfusion analysis switches to another segment. The registration (e.g., tracking quality or alignment) is monitored to determine the time at which to make the switch. For example, the registration of two-dimensional images for a planar region is used to determine when to move to scanning a different planar region (e.g., move to a scan plane with at a different elevation position).

For each segment, an amount of similarity of the ultrasound data obtained at different times (e.g., different frames of data) is used to control the switching to another segment and corresponding destruction transmission of act 36. The transmitting of act 38 is synchronized with the registration such that the transmitting of act 38 occurs where the registration is on one side (e.g., below) a threshold level and does not occur where the registration is on another side (e.g., above) of the threshold level. In one embodiment, a similarity between different frames of data is compared to a threshold. The similarity is between the reference frame and each subsequently acquired frame. If the similarity is higher (e.g., correlation) or lower (e.g., minimum sum of absolute differences) than the threshold, this frame is associated with little motion or displacement relative to the reference frame.

The threshold is predetermined, defined by the user, or adaptive. Predetermined thresholds may be based on experimentation for different imaging applications. User definition allows adjustment of the threshold to provide an image desired by the user. Any adaptive process may be used. For example, contrast agents are allowed to perfuse a region. The user or system then causes destruction by transmitting a higher power beam or beams. The first two frames acquired after destruction are likely similar. This similarity measure with or without an offset (e.g., multiply by 2, 10 or other value or add a value) is used as the threshold for subsequent selection. As another example, a variance between aligned frames of data is used to determine the threshold. Any adaptive threshold is maintained the same for an entire sequence or may adapt throughout the processing of a sequence of frames.

The transmitting of act 38 is gated off where insufficient registration is provided. The lack of registration represents scan region displacement as compared to when the segment was first scanned or scanned at a different time. The threshold registration is an instantaneous measure or is based on a combination of measures. For example, a consecutive number of sequential registrations must satisfy the threshold. As another example, a particular number of registrations in the entire sequence, over a sequence period, or over a particular part of the sequence period occur. Combinations of different thresholds may be used. Any measure of the amount of similarity at one or more times may be used.

For a mechanically steered array, the array is moved in act 36 and the transmissions of act 38 are performed based on synchronization of act 34. If the tracking quality measure indicates good alignment, little motion may be occurring or little displacement has occurred. The array is rapidly mechanically translated to the next elevation position and a new destruction-reperfusion cycle is started. A new tracking or reference frame for use in the next sequence is established. If there is not good alignment, such as due to motion or displacement, the registration of act 32 continues for the current segment. This tracking is monitored until sufficient alignment occurs.

If sufficient alignment does not occur within a set period, the perfusion study may time out and be abandoned since excessive, non-correctable motion has occurred. Alternatively, if substantial amounts of out of plane motion occur between the destruction and reperfusion phases for a given segment, the destruction-reperfusion sequence for that segment is abandoned. The process for the segment is begun again.

The tracking quality information can be obtained over time to determine the period of motion, such as a period of breathing, so that timing information can also be used to determine the best time to translate the mechanical array to avoid intervals of rapid motion associated with the cycle. The reference frame is acquired during a time of lesser motion in one embodiment. The cyclical variation may be used as an additional check, such that the cycle timing indicates less motion occurring and the registration also indicates little displacement.

For an electronically steered array, a similar acquisition sequence—collecting motion tracked frames for a segment—occurs. The destruction and change to a different segment is synchronized to a measurement of good alignment after the reperfusion measurement is performed. An advantage of the electronically steered approach is that rapid switching between segments may occur. A different region may be used for tracking than is being acquired for destruction-reperfusion measurements due to the rapid switching. For example, the center of an organ is scanned for registration of act 32 while obtaining data for a different segment. The start of a destruction-reperfusion sequence for a given two-dimensional slice or other segment is synchronized to good alignment in this center region.

Several portions of a volume may be tracked simultaneously to determine alignment quality. Tracking different portions may help handle cases of rotational motion of an organ.

In act 36, the array is moved. A stepper motor or other device moves the array to a different location. The segment is moved due to the new array position. Where electric steering in the elevation direction is provided, the segment may be moved without moving the array.

After the data for a sequence of scans in a given segment is acquired (e.g., acquiring data for one plane at different times over a reperfusion period), the array and/or segment is moved to scan a different segment. A sequence is acquired sequentially for each segment position. Different segments are scanned at different times.

In act 38, the destruction the contrast agents is performed in a subsequent segment where the correlating indicates a correlation. At the beginning of a new sequence, acoustic energy with an amplitude for destruction of the contrast agents is transmitted. Any amplitude may be used, such as with a mechanical index of 0.6 or higher. Generally, a mechanical index of 1.0 or higher is used to destroy at least some contrast agents. Frequency sweeps or other changes may be used to destroy more contrast agents. Any scan pattern for destruction may be used, such as repeating transmissions along the same scan lines to destroy more contrast agents at deeper depths. Broad or narrow beam transmissions may be used.

A high enough pressure transmit field is generated to destroy agent in the segment in a short period of time, such as 0.5 to 2 seconds. The time for destruction is short enough to allow a parameter related to reperfusion, such as arrival time, to be accurately measured. It is difficult for ultrasound arrays and systems to deliver large amounts of power in a short amount of time to destroy agent over a large region. By performing act 38 for only a sub-set, such as one of two or more (e.g., tens) segments in a volume of interest, sufficiently high pressure for destruction of contrast agents may be provided in a sufficiently short period of time.

The transmitting for destruction is performed as a function of the registration. For a given segment, the process begins with transmission for destruction. The transmission for destruction is not performed until the registration for a previous segment indicates little or no motion or displacement relative to the organ being scanned.

The arrow extending from act 38 to act 30 represents repeating for different segments. For a given segment, obtaining data (act 30) and determining registration (act 32) are repeated to acquire sufficient data for reperfusion study of the segment. Upon completion, the transmission for destruction of act 38 and acts 30-34 are repeated for the next segment. The transmitting occurs a plurality of times. Different transmitting acts transmit the acoustic energy to different portions of the three-dimensional region such that reperfusion information is acquired for the different portions sequentially. Due to the synchronization of act 34, a period between sequential repetitions of the transmitting of act 38 for different segments may vary.

For each repetition or segment, contrast agents in the segment are destroyed prior to obtaining data for reperfusion measurement. Contrast agents are destroyed for each subsequent segment prior to the scanning a plurality of times for the segment and after the scanning of the previous segment.

The three-dimensional reperfusion mapping is acquired as a series of segments, such as two-dimensional slices. This repetition makes three-dimensional volume contrast imaging feasible. Planar or other segment destruction allows enough power to destroy contrast agent by avoiding destruction of contrast agent in the full volume at one time. The reperfusion data of the volume represents local reperfusion capacity rather than perfusion for the entire volume. Global reperfusion may be less useful since the interior portions of the volume or organ may have delayed reperfusion due to destruction of contrast agents in surrounding tissue and blood pools.

Once a complete set of sequences of two-dimensional slices or other segments have been acquired with sufficient registration for destruction and/or reperfusion for all of the segments, the data may be combined to form a complete three-dimensional parametric image. If data for a segment is acquired during undesired motion, the data may be completely rejected. The destruction and reperfusion measurement for the segment may be repeated to acquire sufficient data.

In act 40, only a sub-set (i.e., less than all) of the reperfusion data is selected. One or more frames of data are not selected. The selected frames of data may be used for determining reperfusion parameters without distortion by the unselected data. Alternatively, all of the frames of data for a given segment are used to calculate a reperfusion parameter (i.e., quantity).

The selection is a function of the registration. Generally, the frames of data associated with less inter frame motion are selected, and frames of data associated with more inter frame motion are not selected. The amount of similarity associated with a frame of data indicates whether the frame of data should be maintained or included in the reperfusion analysis. Tracking information is acquired prior to and after destruction as well as during the reperfusion measurement. Frames of data are selected as long as excessive motion has not occurred. If sufficient tracking is maintained across the destruction events and at least a particular percentage of the time during the reperfusion measurement, then that segment is sufficient. If the registration indicates motion for a portion of the sequence for a given segment, the frames acquired during that portion or portions may be discarded or not used. Different thresholds may be used depending on the type of reperfusion measurement. For example, poor registration during a middle of the sequence period for measuring time to reperfuse may be acceptable, but not for measuring a rate of reperfusion. Different thresholds may be used for different portions of the segment period.

If an insufficient number of frames of data are available after selection, the reperfusion measurement may be repeated for the segment. Good tracking quality is provided for enough time during the reperfusion measurement to ensure that the desired parameter can be measured with sufficient accuracy.

The selection is based on frames without motion correction. Alternatively, the frames are motion corrected and the registration after correction is used for selection. The motion compensation or correction may be performed before or after selection. For example, the same similarity or displacement calculation is used for selection and motion correction. After determining displacement based on similarity or other information, the frames of data are spatially aligned. Rigid or non-rigid correction may be used. The alignment more likely avoids blurring.

In act 42, a quantity is calculated from the ultrasound data representing the reperfusion. The reperfusion quantity is a function of the data distributed along three spatial dimensions in the three-dimensional region, a function of data for one location, a function of one-dimensional distribution of data or a function of a two-dimensional distribution of data. Information from the selected subset of frames and not from unselected ones of the ultrasound frames of data is combined. The combination is for any now known or later developed inter-frame processing, such as maximum intensity holding, minimum intensity holding, mean determination, or constructing one or more time intensity curves. Parameter data for the volume is generated as a function of data from the selected frames. The selected frames of ultrasound data are integrated as a function of time to determine the parameter values for each location. Integrated includes mathematical integration or forming an image from a plurality of sources.

For each spatial location of a region of interest, the data is compared or used to determine a value. For each voxel, a value is selected as a function of data from each of the remaining (selected) frames of data. For example, the mean, median or other statistical value of data for each spatial location as a function of time is determined from the frames. As another example, the maximum, minimum, or other data in relation to data of the selected frames is selected based on comparison. The frames of the selected subset are combined into a persisted frame or single frame. In another example, a curve representing intensity or other contrast agent response as a function of time is determined from the frames. The curve is for a region or for a spatial location. Since the frames are associated with different times, the curve is of intensity as a function of time. A characteristic of the curve may be determined as the parameter. In yet another example, a time for sufficient contrast agent response to return to the spatial location is calculated.

The data combined is of the same or different type of data used for selection. For example, contrast agent specific or related data is integrated. A different type of data, such as B-mode data with or without the contrast agent specific data is used for selection.

In act 44, an image is generated. The image is a function of a level of contrast agent after destruction (e.g., a function of the calculated parameter values). By combining information from contrast agents, such as information primarily at a cubic fundamental of ultrasound signals, the perfusion of contrast agents and/or small vasculature may more easily be viewed. Any perfusion parameter may be calculated for each spatial location, such as time to perfuse or mere intensity of contrast agent. The selected data (and not unselected data) or all of the data for a given voxel is used to determine the perfusion parameter. The image may represent a maximum return from contrast agents over the sequence period or other parameter of reperfusion. The perfusion parameter information is used as voxel data for rendering the image. The image is a rendering with pixels modulated as a function of a perfusion level for the portion of the region represented by the respective pixel.

The image is rendered from the data representing the volume. The parameter (quantity) for each spatial location in the volume (i.e., each voxel) is used for rendering. Surface or projection rendering may be used. For projection rendering, maximum, minimum, averaging or other projection may be used. Alpha blending may be used. The rendering of the volume may be with or without opacity weighting and/or shading. Any now known or later developed rendering of the volume may be used. In alternative embodiments, a cut-plane image or multiplanar reconstruction images are generated from the reperfusion data of the volume.

The reperfusion rendering may be viewed alone or separately. Alternatively, the reperfusion information is overlaid or blended with a rendering from other data, such as tissue (e.g., B-mode) or flow (e.g., Doppler velocity or energy).

In an alternative or additional embodiment, a quantity is displayed. The quantity is a number or text, such as "1.4 seconds." A graph, such as average contrast agent in a region as a function of time, may be displayed. One or more time-intensity curves may be displayed, such as different curves derived from local averages at different regions in the volume.

Figure 2:
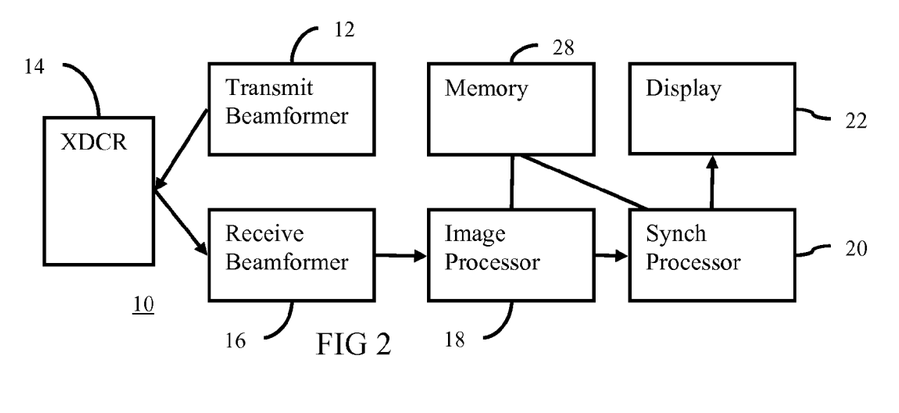
FIG. 2 is a block diagram of one embodiment of an ultrasound imaging system for motion synchronized destruction for reperfusion.

FIG. 2 shows a system 10 for motion synchronized destruction for reperfusion in medical diagnostic ultrasound. The system 10 includes a transmit beamformer 12, a transducer 14, a receive beamformer 16, an image processor 18, a synchronization processor 20, a display 20, and a memory 28. Additional, different, or fewer components may be provided. For example, a separate memory is provided for buffering or storing frames of data over time. As another example, the synchronization processor 20 is combined with or part of the image processor 18. The synchronization processor 20 may be separate processors, such as one for controlling scanning and another for rendering an image.

The system 10 is a medical diagnostic ultrasound imaging system in one embodiment, but other imaging systems of the same (ultrasound) or different modality may be used. In other embodiments, part or all of the system 10 is implemented in a computer or workstation. For example, previously acquired frames of data are processed without the beamformers 12, 16 or transducer 14.

The transmit beamformer 12 is an ultrasound transmitter, memory, pulser, analog circuit, digital circuit, or combinations thereof. The transmit beamformer 12 is operable and configured to generate waveforms for a plurality of channels with different or relative amplitudes, delays, and/or phasing. Upon transmission of acoustic waves from the transducer 14 in response to the generated waves, one or more beams are formed. The transmit beamformer 12 may cause the beam to have a particular phase and/or amplitude. For example, the transmit beamformer 12 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used.

The transducer 14 is a 1-, 1.25-, 1.5-, 1.75- or 2-dimensional array of piezoelectric or capacitive membrane elements. Two-dimensional arrays provide electronic steering in azimuth and elevation with or without equal numbers of elements along both dimensions. The two-dimensional array may be flat or curved. The transducer 14 includes a plurality of elements for transducing between acoustic and electrical energies. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

Any desired sequence of transmit and receive operation may be used to obtain ultrasound information. For example, B-mode data may be obtained by scanning a segment once. The B-mode may be used for tissue imaging. Correlation or motion tracking may be used to derive fluid information from B-mode data. B-mode operation may provide contrast agent information. Doppler information may be obtained by transmitting sequences of beams along each scan line. A corner turning memory may be used to isolate tissue, contrast agents, and/or flow information from Doppler signals. Other now known or later developed modes may be used.

In one embodiment, the mode is a contrast agent imaging mode. Contrast agents may be imaged with typical B-mode or Doppler techniques. Isolating information at the second, even, odd, sub, or other harmonics may more likely identify information from contrast agents. For example, a two pulse technique is used. The pulses have a same amplitude, but different phase. By summing the response, information associated with even harmonics is identified. Filtering may alternatively be used. Alternatively or additionally, relative phasing is provided in the receive processing.

In one embodiment, the transmit sequence is controlled to generate echo signals responsive to the cubic fundamental. The beamformer 12 is operable to transmit a plurality of pulses having at least two different amplitude levels and at least two of the plurality of pulses having opposite or different phases. Transmitter power can be varied in any suitable manner, as for example by adjusting the voltage applied to individual transducer elements, or by adjusting the number of transducer elements (or transmit aperture) used to form a particular pulse.

For obtaining ultrasound data at the cubic fundamental, the receive beamformer 16 includes line memories and a summer or a filter to combine signals responsive to the transmissions. The line memories or buffers can be formed as physically separate memories, or alternately they can be formed as selected locations in a common physical device. The beamformed signals are stored in the line memories or buffers and then weighted and summed in a weighted summer. Weighting values for both amplitude and phase are used in the weighted summer. The memories and the summer can be implemented using analog or digital techniques. The weighted summer forms a composite output signal by weighting the separate beamformed receive signals. The composite output signal for a given spatial location is a sample associated with the cubic fundamental response.

Obtaining cubic fundamental information is disclosed in U.S. Pat. No. 6,494,841, the disclosure of which is incorporated herein by reference. Any of the transmit sequences and receive combinations disclosed therein may be used for obtaining cubic fundamental information. Other transmit sequences and receive combinations for obtaining cubic fundamental information may be used, such as disclosed in U.S. Pat. Nos. 6,602,195, 6,632,177, 6,638,228 and 6,682,482, the disclosures of which are incorporated herein by reference. In general, a sequence of pulses with different amplitudes and phases are transmitted. Using amplitude change or different amplitudes without different phases may also be used to obtain cubic fundamental information. By combining received signals responsive to the sequence, a sample including cubic fundamental information is obtained. The cubic fundamental information is highly specific to ultrasound contrast agents since contrast agents produce cubic response and the transducer and tissue produce very little cubic response. The information provides tissue clutter rejection, allowing for imaging more specific to contrast agents. For example, small vessels within tissue may be more easily imaged or identified using cubic fundamental information.

The image processor 18 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting information for display from beamformed ultrasound samples.

In one embodiment, the image processor 18 implements a fast Fourier transform from a plurality of samples representing a same region or gate location. Each of the samples is responsive to cubic fundamental so that a pulsed wave Doppler display may be generated from cubic fundamental information. The image processor 18 also includes a B-mode detector in a parallel track. The B-mode detector operates on the same or different beamformed samples to detect tissue, contrast agent, or tissue and contrast agent response. For example, one receive beam for each spatial location from the sequence of receive beams used for cubic fundamental isolation is applied to the B-mode detector for imaging primarily tissue information.

The image processor 18 outputs frames of ultrasound data. The frames of data are formatted in an acquisition format (e.g., polar coordinate), a display format (e.g., scan converted into a Cartesian coordinate format or an image), or other format. Each frame of data represents a one, two, or three-dimensional scanned region. The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

In an alternative embodiment, the image processor 18 loads data from a network or memory. For example, DICOM or other images are loaded. Each image is a frame of data. One frame may include different types of data, one overlaid on another. Alternatively, each frame includes only one type of data with different frames for different data types. In another embodiment, each frame is subdivided so that one portion includes one type of data and another portion includes another type of data.

The synchronization processor 20 is an application specific integrated circuit, correlation processor, Fourier transform processor, general processor, control processor, field programmable gate array, digital signal processor, analog circuit, digital circuit, graphic processing unit, combinations thereof, or other now known or later developed device for determining similarity and/or displacement between frames of data. The synchronization processor 20 receives the frames of data to determine the timing for switching between segments for scanning and for transmitting destruction pulses.

The synchronization processor 20 or the image processor 18 determines reperfusion parameters for each spatial location. In one embodiment, a maximum intensity of return from contrast agent over the sequence of scanning is determined by a persistence filter. Data for a particular spatial location may be compared from one frame to another frame or an ongoing combination frame. Based on the comparison (e.g., highest value, contribution to mean value, or lowest value), one of the values is selected or the ongoing combination frame is updated to include the desired value. The data from frames for a same location may be combined to determine a perfusion parameter, such as determining an average contrast agent level or determining a characteristic of a time-intensity curve.

The synchronization processor 20 may also include a rendering processor, graphics processing unit, alpha blending buffer, other buffer, memory, processor, adder, or other device for generating an image from information of a volume set of data or reperfusion parameter values. The synchronization processor 20 renders an image representing a volume.

The display 20 is a CRT, monitor, LCD, flat panel, projector or other display device. The display 20 receives display values for displaying an image. The display values are formatted as a one-dimensional image, two-dimensional image, or three-dimensional representation. In one embodiment, the display values are for an image generated as a function of frames of data acquired at different times. As additional frames of data are acquired and selected, the image may be updated. Other images, such as images from single or component frames of data, may also be displayed.

The display 20 may display an image rendered from perfusion information in three-dimensions. The perfusion information is determined by local destruction and reperfusion measurements. The measurements are repeated for different portions of a volume. The acquired data represents the reperfusion for the volume despite being sequentially acquired for the different segments. The data is rendered to represent reperfusion for the volume from a selected viewing angle or arbitrary cut-plane.

The image processor 18 and/or synchronization processor 20 operate pursuant to instructions. A computer readable storage medium, such as the memory 28, stores data representing instructions executable by one or both of these programmed processors for motion synchronized destruction for reperfusion in medical diagnostic ultrasound. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for motion synchronized destruction for reperfusion in medical diagnostic ultrasound, the method comprising:
  acquiring a plurality of ultrasound frames of data, representing, at least in part, information from contrast agents in a three-dimensional region of a patient;
  determining a registration level as a similarity between data from different times within the plurality;
  transmitting, at a time during acquiring the plurality, acoustic energy with an amplitude for destruction of the contrast agents;
  synchronizing the transmitting with the registration level such that the transmitting occurs where the registration level is on a first side of a first level of the registration and does not occur where the registration level is on a second side of the first level of the registration; and
  generating an image as a function of a level of contrast agents, the level of contrast agents being of the contrast agents after the transmitting.

2. The method of claim 1 wherein acquiring the plurality comprises acquiring the ultrasound frames of data for a first plane over a first period, the registration being between the ultrasound frames of data for the first plane.

3. The method of claim 2 wherein acquiring comprises acquiring the ultrasound frames of data for a second plane, different than the first plane, after the transmitting, the registration switching to being between the ultrasound frames of data for the second plane and a subsequent transmitting being a function of the registration for the second plane.

4. The method of claim 1 wherein determining the registration level comprises determining a similarity between the ultrasound frames of data.

5. The method of claim 1 wherein determining the registration level comprises determining for a sub-volume of the three-dimensional region of the patient.

6. The method of claim 1 wherein acquiring comprises acquiring with a mechanically translated one-dimensional array, the mechanical translation being in steps, where the acquiring, determining, transmitting and synchronizing are performed for each of the steps of translation of the mechanically translated one-dimensional array.

7. The method of claim 1 wherein acquiring comprises acquiring with a multi-dimensional array of elements electronically steered in azimuth and elevation dimensions.

8. The method of claim 1 wherein determining comprises tracking motion with a first occurring one of the ultrasound frames of data being a reference frame for the tracking motion of a plurality of subsequent ones of the ultrasound frames of data.

9. The method of claim 1 wherein acquiring comprises acquiring over a physiological cycle greater than two seconds, the three-dimensional region of the patient being other than a heart, variation in the registration being primarily due to breathing motion, movement of the patients skin adjacent a transducer, movement of the transducer or combinations thereof.

10. The method of claim 1 wherein generating the image comprises displaying a reperfusion quantity, the reperfusion quantity being a function of the data distributed along three spatial dimensions in the three-dimensional region.

11. The method of claim 1 wherein generating the image comprises displaying a rendering with pixels modulated as a function of the level of the contrast agents for a portion of a region represented by the respective pixel.

12. The method of claim 1 wherein synchronization comprises gating off the transmitting where a first number of registrations in a period, a second number of sequential registrations, or combinations of the first and second number correspond to an amount of correlation below the first level of the registration.

13. The method of claim 1 further comprising repeating the determining and transmitting during the acquiring of the plurality, a period between sequential repetitions of the transmitting varying due to the synchronization.

14. The method of claim 1 wherein transmitting comprises transmitting a plurality of times during the acquiring of the plurality, different transmitting acts transmitting the acoustic energy to different portions of the three-dimensional region such that reperfusion information is acquired for the different portions sequentially.

15. The method of claim 1 further comprising:
  selecting a sub-set of the ultrasound frames of data, the selecting being a function of the registration level;
  wherein generating the image comprises generating the image from the data of the sub-set and not from data outside the sub-set.

16. In a non-transitory computer readable storage medium having stored therein data representing instructions executable by a programmed processor for motion synchronized destruction for reperfusion in medical diagnostic ultrasound, the storage medium comprising instructions for:
  generating acoustic energy for destruction of contrast agents, the generating being sequentially performed for different segments of a three-dimensional volume of a patient;
  obtaining ultrasound data representing reperfusion of contrast agents within each of the different segments, the obtaining for each segment being performed after the generating for the respective segment; and
  controlling the generating of the acoustic energy for destruction for each segment based on an amount of similarity of the ultrasound data obtained at different times.

17. The non-transitory computer readable storage medium of claim 16 wherein obtaining comprises obtaining with a mechanically translated array, the different segments corresponding to the array at different positions for respective different scan planes, the instructions further comprising:
  moving the array after obtaining the data with scans of the respective scan plane at different times for each of the segments;
  wherein controlling comprises calculating the amount of similarity for the respective scan plane at the different times, and changing the position of the array and corresponding scan plane where the amount of similarity is higher than a threshold.

18. The non-transitory computer readable storage medium of claim 16 wherein obtaining comprises obtaining with a multi-dimensional array of elements, the ultrasound data obtained and the acoustic energy generated with electrical steering in azimuth and elevation directions, the electrical steering used to obtain the data for the different segments, wherein controlling comprises calculating the amount of similarity for the respective segment at different times, and changing the segment being scanned where the amount of similarity is higher than a threshold.

19. The non-transitory computer readable storage medium of claim 16 further comprising instructions for:
calculating a quantity from the ultrasound data representing the reperfusion;
selecting less than all of the ultrasound data for a first segment of the different segments to calculate the quantity, the selecting being a function of the amount of similarity associated with the ultrasound data.

20. A method for motion synchronized destruction for reperfusion in medical diagnostic ultrasound, the method comprising:
scanning, with ultrasound from a transducer, first and second different portions of a volume of a patient, the first portion scanned a first plurality of times and then the second portion scanned a second plurality of times;
destroying contrast agents in the first portion prior to the scanning of the first plurality of times;
destroying contrast agents in the second portion prior to the scanning of the second plurality of times and after the scanning of the first portion;
correlating data representing the first portion from the first plurality of scans;
performing the destroying of the contrast agents in the second portion where the correlating indicates a threshold amount of correlation.

* * * * *